(12) United States Patent
Hasebe et al.

(10) Patent No.: US 6,284,463 B1
(45) Date of Patent: Sep. 4, 2001

(54) METHOD FOR DETECTION OF MUTATIONS

(75) Inventors: Masahisa Hasebe, Nara-ken; Masanori Goto; Mariko Tosu, both of Tokyo, all of (JP)

(73) Assignee: Amersham Pharmacia Biotech AB, Uppsala (SE)

( * ) Notice: Subject to any disclaimer, the term of this patent is extended or adjusted under 35 U.S.C. 154(b) by 0 days.

(21) Appl. No.: 09/194,478

(22) PCT Filed: May 22, 1997

(86) PCT No.: PCT/SE97/00839

§ 371 Date: Aug. 18, 1999

§ 102(e) Date: Aug. 18, 1999

(87) PCT Pub. No.: WO97/45555

PCT Pub. Date: Dec. 4, 1997

(30) Foreign Application Priority Data

May 29, 1996 (SE) ................................. 9602062

(51) Int. Cl.[7] .............. C12G 1/68; C12N 9/22; C12P 19/34; C07H 21/04; C07H 21/02
(52) U.S. Cl. ................ 435/6; 435/91.1; 435/91.2; 435/196; 435/197; 435/199; 435/287.2; 435/288.3; 435/288.7; 536/23.1; 536/24.1; 536/24.33; 536/25.32
(58) Field of Search .................. 435/6, 810, 91.2, 435/91.1, 196, 197, 199; 536/23.1, 24.33, 24.1, 25.32; 436/809

(56) References Cited

U.S. PATENT DOCUMENTS 6,013,431 * 1/2000 Soderlund et al. ............... 435/5

FOREIGN PATENT DOCUMENTS

WO 85/05685 * 12/1985 (WO).
WO 93/02216 * 12/1985 (WO).
WO 97/45555   12/1997 (WO).

OTHER PUBLICATIONS

Jonsson et al. Real–Time Biospecific Interaction analysis using Surface Plasmon Resonance and a Sensor Chip Technology. BioTechniques Vlume 11, No. 5, pp. 625–627, Dec. 1991.*
Ahern, H. Biochemical, Reagent Kits offer Scientists Good Return on Investment. The Scientist vol. 9, No. 15, pp. 1–5, Jul. 1995.*

* cited by examiner

*Primary Examiner*—Stephanie W. Zitomer
*Assistant Examiner*—Cynthia B. Wilder
(74) *Attorney, Agent, or Firm*—Royal N. Ronning, Jr.

(57) ABSTRACT

A method and a kit for detecting a mutation from a non-mutated sequence of a target polynucleotide in a sample, by using a mismatch binding protein. The method comprises: a) providing non-mutated and mutated target polynucleotide; b) forming duplex of the non-mutated and mutated single strands of the target polynucleotide in a); c) adding a single strand binding protein to the polynucleotide from b); d) incubating the mismatch binding protein with an activating agent; e) adding the incubated mismatch binding protein from d) to the polynucleotide from c), whereby the mismatch binding protein binds to the duplex formed by one non-mutated and one mutated single strand of the target polynucleotide; f) detecting the presence of any mismatch binding protein bound to the target polynucleotide. The kit comprises: a) single strand binding protein, b) activator for mismatch binding protein; c) mismatch binding protein; d) amplification primer(s); e) solid support for binding of target polynucleotide or mismatch binding protein.

13 Claims, 4 Drawing Sheets

METHOD FOR DETECTION OF MUTATIONS

Figure 1A:
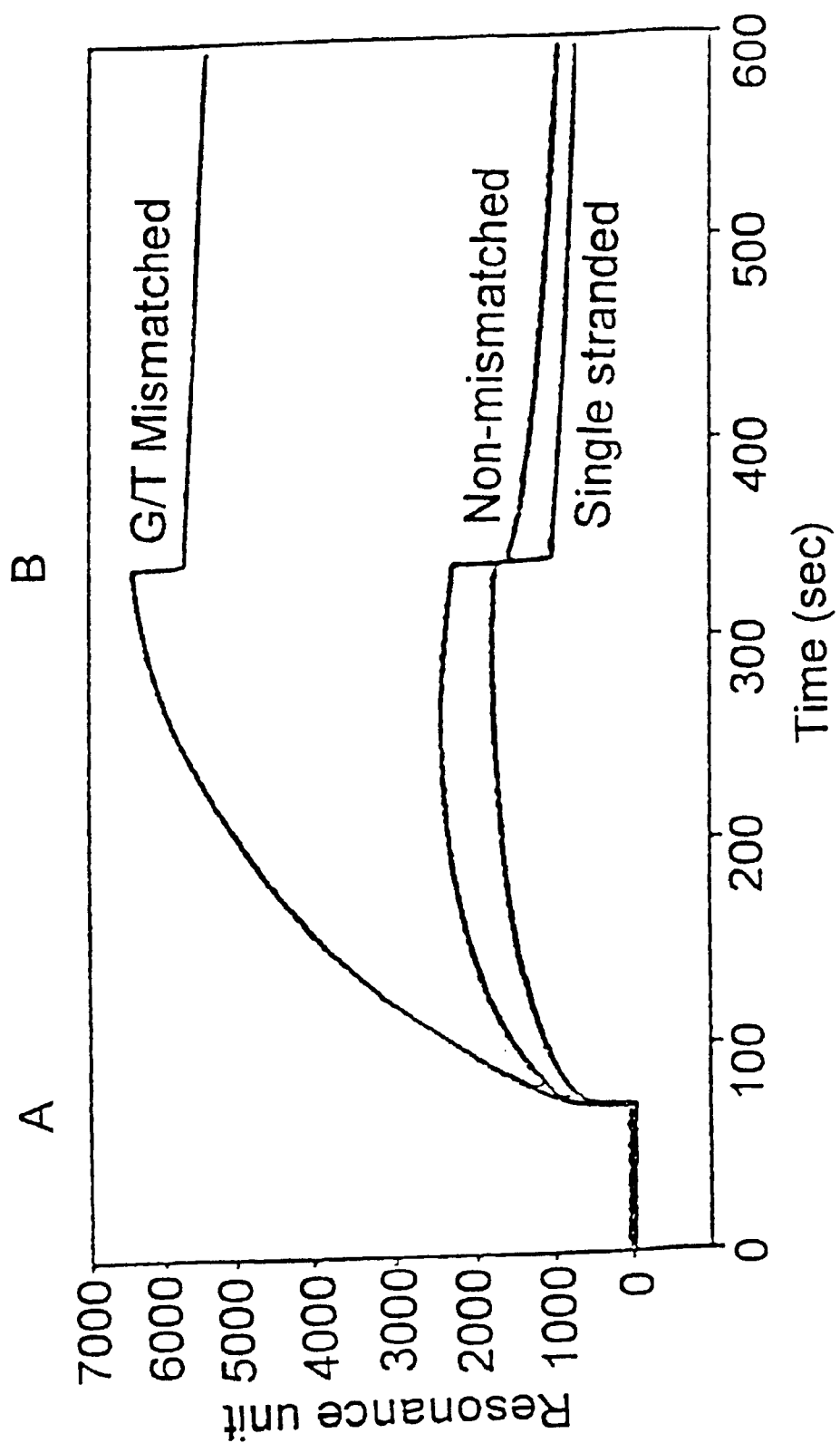

The present invention relates to a method and a kit for detecting a mutation from a non-mutated sequence of a target polynucleotide. More specifically the invention relates to a method for detecting mutations by using a mismatch binding protein.

The development of methods for the detection of mutations in DNA is important in diagnostic tests since a large number of human genetic diseases are caused by single base substitutions or by small additions or deletions in the genome. For example, the possibility to detect mutations is an important tool in early detection of cancer.

There are a lot of methods available for detection of mutations. Single strand conformation polymorphism (SSCP)for example, is based on the fact that single stranded DNA that differs by as little as a single base can take up different conformations in a non-denaturing environment, which allows for separation by electrophoresis. In Denaturing gradient gel electrophoresis (DGGE) the altered melting characteristics, exhibited by base pair changes, are used. The melted duplexes are separated when moving into a gel of increasing denaturation concentration. These methods as well as others require gel electrophoresis separation.

Many methods worked out to detect mutations, consisting of one or a few bases, are based on hybridization between a standard DNA (or RNA) and a test DNA. The test sample is mixed with wild-type sample, which can be labelled, and the mixture is denatured and allowed to renature. The mutation is then exposed as a mispaired or unpaired base in a heteroduplex molecule. Different ways are known for the detection of the mispaired or unpaired base. Cleaving of by chemical or enzymatic treatment is one commonly used method. The fragments are observed by gel electrophoresis. Several patent applications describe the use of mismatch binding proteins to detect the heteroduplex molecule (e.g. WO 93/02216, WO 95/12689). DNA mispairing occurs in vivo and is recognized and corrected by a family of repair proteins. Included are proteins which recognize and bind to mismatch containing DNA, so called mismatch binding proteins. It has been found that the mismatch binding proteins forms specific complexes with any of the eight possible mismatched base pairs. The mismatch repair system has been studied in bacteria such as *E.coli* and Salmonella. MutS is one such protein identified in the *E.coli* mismatch repair system. The detection of binding of a mismatch binding protein to the DNA is usually made by some type of a label. Recently a rapid method for detection of point mutations using a label free technique was reported (by Ivan Babic et al on the 5$^{th}$ BIA symposium in San Diego, September 1995). The interaction of MutS with short oligonucleotides containing various base-pair mismatches was examined using optical biosensor technology.

The detection methods according to the state of the art based on gel electrophoresis or labelling procedures are time-consuming methods. Therefore, in developing a time-effective assay, these methods are difficult to apply for rapid screening of samples for the detection of mutations. These methods are also difficult to automate.

According to WO 95/12689 and also to Babic et al as mentioned above, MutS binds to DNA containing mispaired bases, but does not bind to DNA without mismatches or single stranded DNA. However, it was found in the present invention that MutS binds non-specifically. Thus, it was found that MutS binds both to single stranded DNA and to double stranded DNA without mismatches. This means that the accuracy of the MutS detection method is not satisfactory for detection of mutations, because non-specific binding of MutS can cause false positive.

The object of the present invention is to obtain an improved method for detecting a mutation by using a mismatch binding protein, without the draw-back mentioned above.

A further object of the invention is to present a kit useful for detection of mutations.

The objects of the invention are achieved by the method and kit as claimed in the claims. According to the invention a method for detecting a mutation from a non-mutated sequence of a target polynucleotide in a sample is obtained by using a mismatch binding protein. The method comprises:

a) providing non-mutated and mutated target polynucleotide,
b) forming duplex of the non-mutated and mutated single strands of the target polynucleotide in a),
c) adding a single strand binding protein to the polynucleotide from b),
d) incubating the mismatch binding protein with an activating agent,
e) adding the incubated mismatch binding protein from d) to the polynucleotide from c), whereby the mismatch binding protein binds to the duplex formed by one non-mutated and one mutated single strand of the target polynucleotide,
f) detecting the presence of any mismatch binding protein bound to the target polynucleotide.

According to a further aspect of the invention a kit for detecting a mutation from a non-mutated sequence of a target polynucleotide in a sample is achieved. The kit comprises:

a) single strand binding protein,
b) activator for mismatch binding protein,
c) mismatch binding protein,
d) amplification primer(s),
e) solid support for binding of target polynucleotide or mismatch binding protein.

With the present invention it was surprisingly found that the non-specific binding of mismatch binding protein could be avoided. Binding of the mismatch binding protein to single strands is inhibited by the single strand binding protein. By activating the mismatch binding protein with an activator, before addition to the sample, binding to double strands lacking mismatches does not take place.

According to a preferred embodiment of the invention, the mutated or the non-mutated target polynucleotide is immobilized on a solid support before the duplex in step b) is formed. Most preferably the non-mutated target nucleotide is immobilized. Alternatively, the target polynucleotide is immobilized on the solid support after duplex formation in step b) or mismatch binding protein is immobilized on a solid support and binding of the target polynucleotide is detected. According to a further preferred embodiment the solid support is a sensor chip surface. The presence of the mismatch binding protein can then be detected by a label free technique. One such method is detection by surface plasmon resonance (SPR). An optical biosensor system based on SPR is described in WO 90/05295 filed by Pharmacia AB. By this method of detection the time-consuming detection with gel electrophoresis or labelling could be avoided.

In the first step of the invention a sample of the target polynucleotide, i.e. a sequence of a DNA or RNA having a mutation, is mixed with a non-mutated (wild-type) sample of the polynucleotide. The sample mixture is denatured to achieve single strands of the polynucleotide, if the samples are not already single stranded and then the single strands are allowed to renature to double strands. There will then be formed homoduplexes as well as heteroduplexes. A homoduplex is a duplex of two non-mutated strands or two mutated strands. A heteroduplex is a duplex of one non-mutated and one mutated strand. According to one embodiment of the invention the target polynucleotide in the sample can be amplified before the first step of the invention. Conventional amplification methods can be used, especially amplification by PCR (see U.S. Pat. No. 4,683,195; U.S. Pat. No. 4,683,202; U.S. Pat. No. 4,800,159).

In one preferred embodiment a single stranded non-mutated polynucleotide is immobilized to a sensor chip surface and the sample suspecting of containing a mutation of the polynucleotide is added in single stranded form. The added sample is allowed to anneal to the polynucleotide on the sensor chip.

In the next step a single strand binding protein is added which binds to the single strands being left in the mixture. Before the mismatch binding protein is added to the thus produced sample mixture, the mismatch binding protein is incubated with an activator. It was found that by activating the mismatch binding protein the binding to homoduplexes is prevented. The activated mismatch binding protein is added to the sample mixture and allowed to bind to the heteroduplex. The presence of any bound mismatch protein is then detected.

The immobilization of the polynucleotide is made by conventional methods such as adsorption, covalent binding or some type of a binding pair. One member of that binding pair is attached to the polynucleotide or to the mismatch binding protein and the other member is applied to the solid support. Example of such binding pairs are biotin—avidin, biotin—streptavidin, cystein—thiol groups, antigen—antibody, lectin—sugar. In a preferred embodiment of the kit the amplification primer(s) or the mismatch binding protein has/have one member of a binding pair attached and the other member of the binding pair is coated on the solid support.

The single strand binding proteins (SSB) used to inhibit the binding of the mismatch protein to single strands could be any of the SSB known in the art. Preferred compounds are single strand binding protein (from $E.coli$, fruit fly, $Xenopus\ laevis$) and gene 32 protein from T4 bacteriophage and their homologue from other species.

The mismatch binding protein used is one of MutS, HexA, MSH1–6, Rep3, RNaseA, uracil-DNA glycosilase, T4 endonuclease VII, resolvase, a protein which can bind to the mismatch. Before adding the mismatch binding protein to the polynucleotide duplex, the protein is activated with an activating agent. Preferably the activating agent is one of the compounds ATP (adenosine 5'triphosphate), ADP (adenosine 5'diphosphate), ATP-γ-S (adenosine 5'-O-(3-thiotriphosphate), AMP-PNP (adenosine 5'-[β, γ-imido] triphosphate) or a nucleotide which can bind to the mismatch binding protein. By this activating of the mismatch binding protein it was found that the non specific binding to both non-mutated as well as mutated samples was avoided. The activation is made by incubating the mismatch binding protein with the activating agent at ambient temperature for seconds to minutes. Finally the activated protein is added to the polynucleotide mixture.

The detection of the bound mismatch protein can be made by the conventional methods used in the state of the art.

However, a preferred method is to use an optical biosensor system according to WO 90/05295, as mentioned above and which is incorporated herein by reference. An optical biosensor provides a simple and easy method to detect mutations and permits automation of systems for clinical applications and diagnostic screening. One such system is BIAcore® (Pharmacia Biosensor AB, Uppsala, Sweden), which is based on WO 90/05295.

The invention will now be illustrated with the following non-limiting examples. With parts and per cent are meant parts by weight and per cent by weight if not differently stated. In the examples the result is presented in FIGS. 1–3 with the meaning:

FIG. 1A: A graph of the binding of MutS to oligonucleotides, both double stranded, non-mismatched and mismatched as well as single stranded. The binding is represented in the form of resonance units from the surface plasmon resonance (SPR). MutS is introduced at A and the buffer at B in the figure.

Figure 1B:
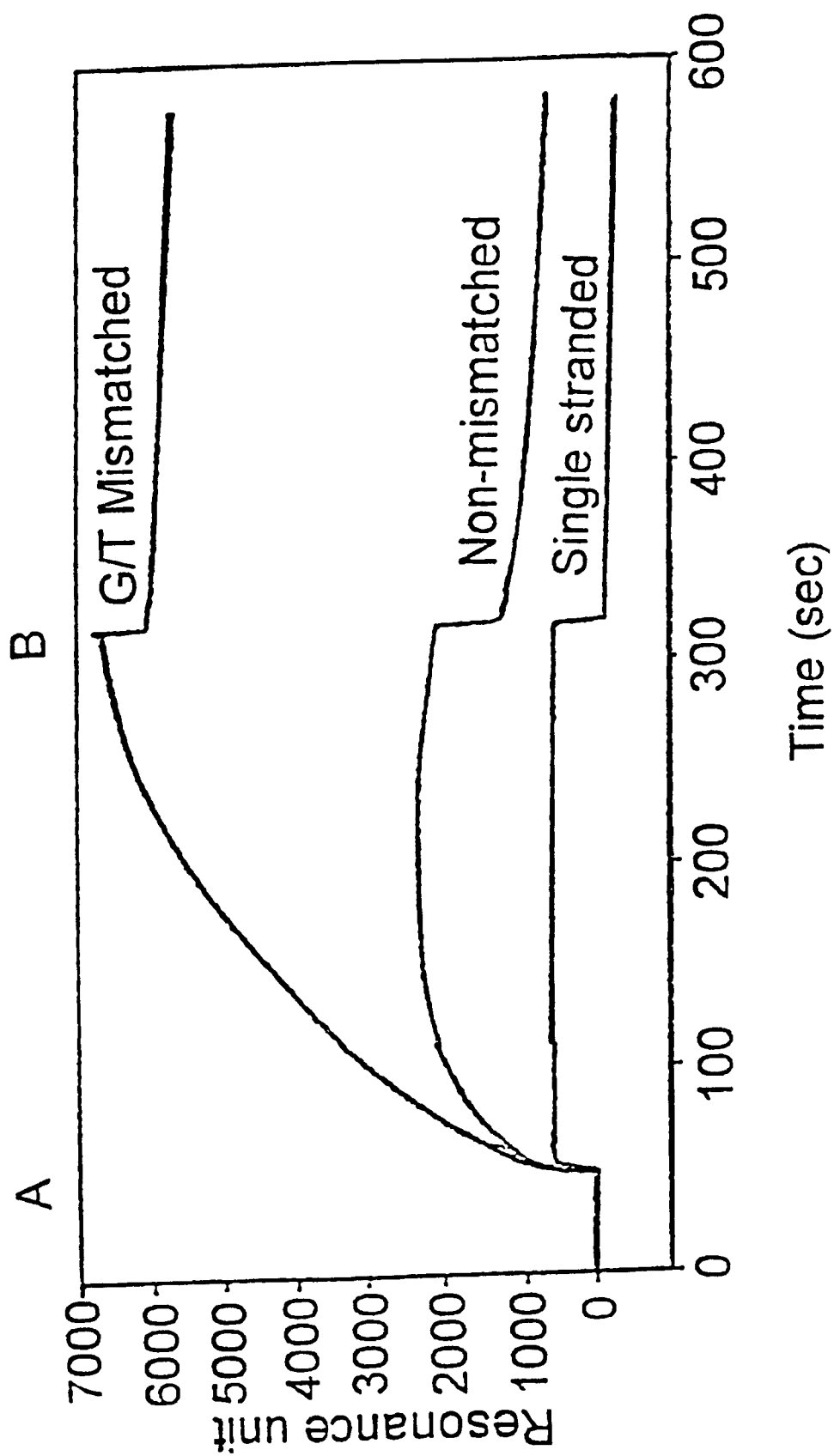

FIG. 1B: A graph as in FIG. 1A but where the binding of MutS to single stranded DNA has been blocked.

Figure 2:
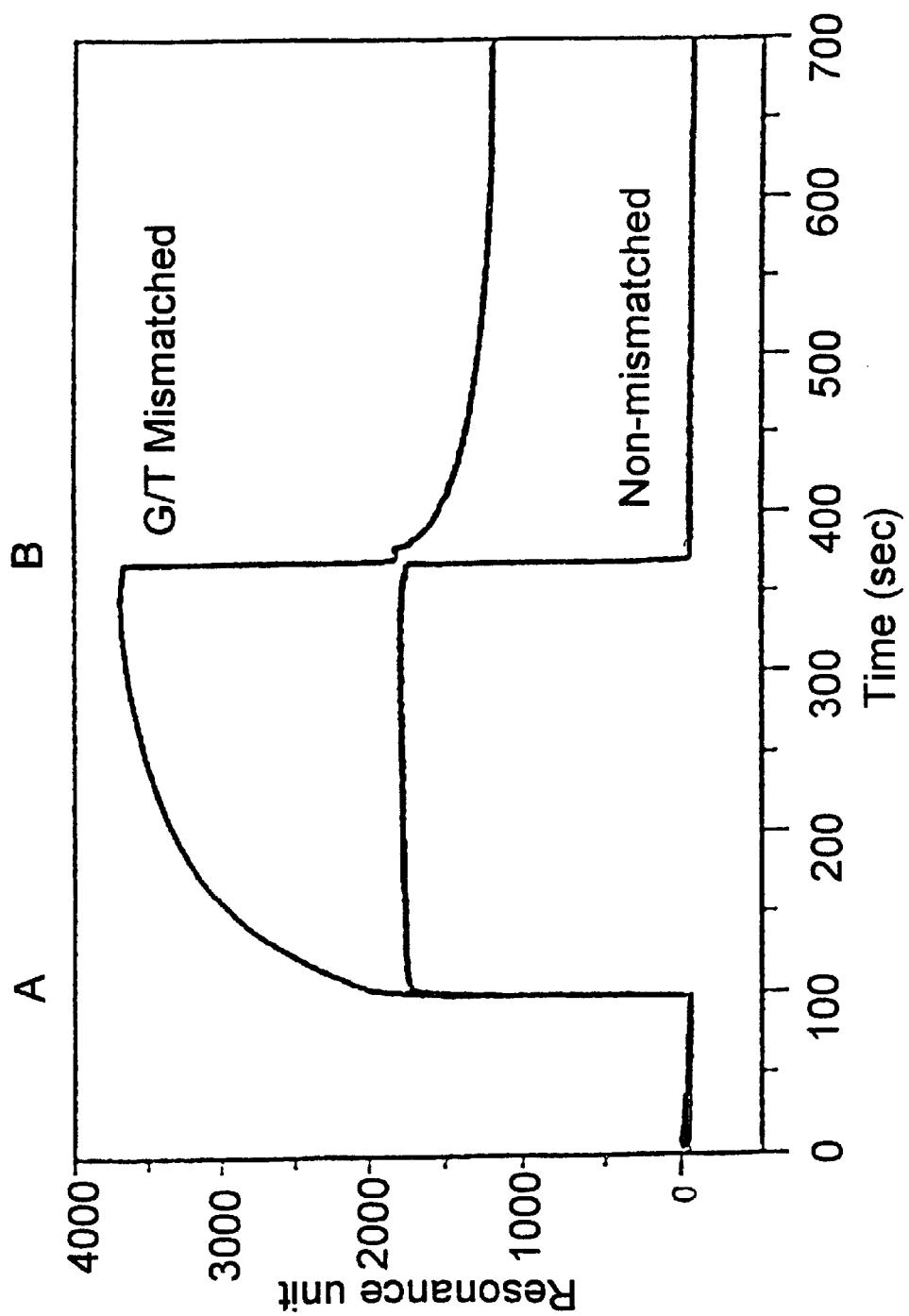

FIG. 2: A graph of the binding of MutS according to the invention. The binding is represented as in FIGS. 1A and 1B.

Figure 3:
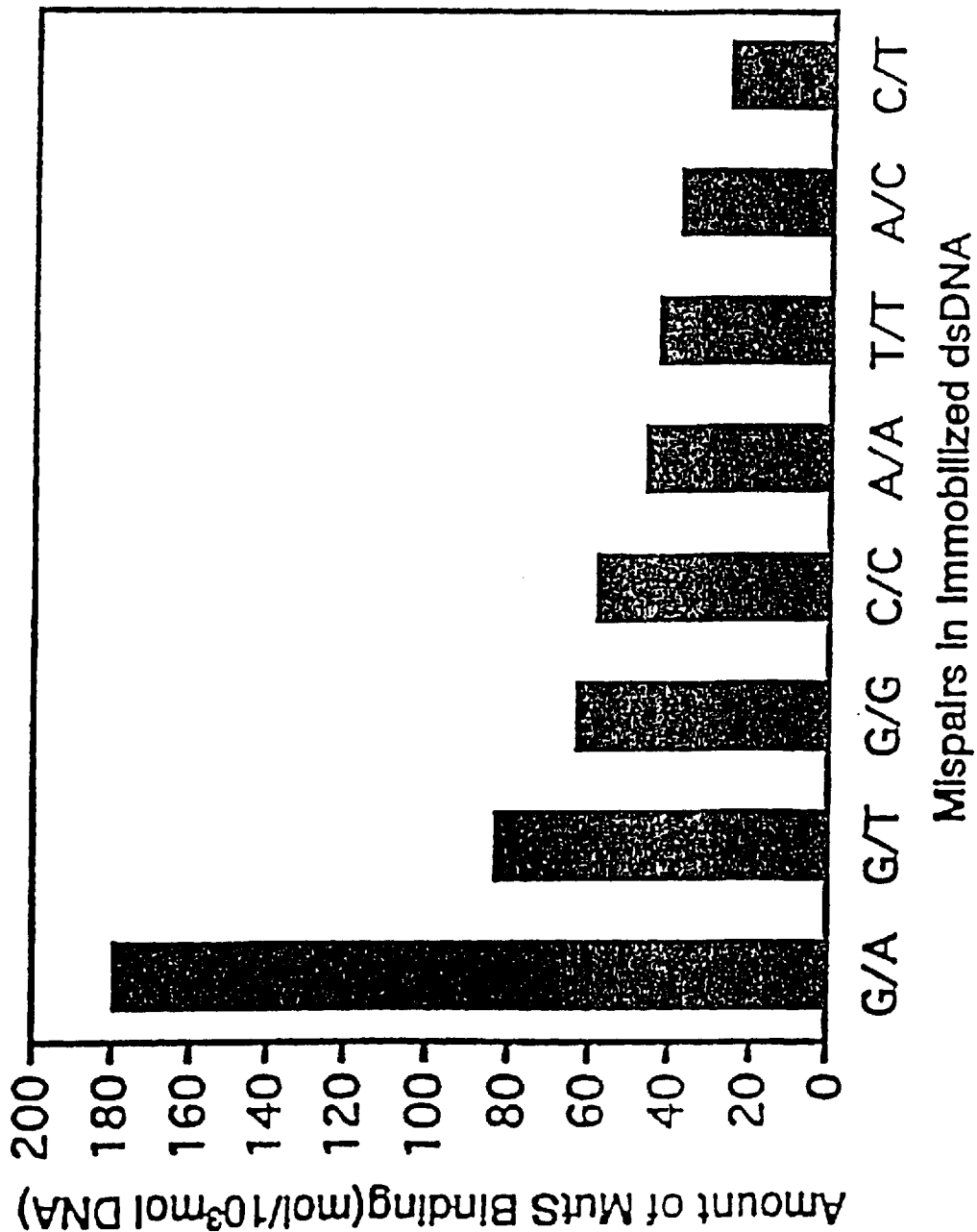

FIG. 3: The amount of MutS binding for the different kinds of mispairs as shown in table 2 in the sequence listing.

EXAMPLE 1

Immobilization and Formation of Duplex

A sensor chip for optical detection was used. The chip comprises a transparent plate of glass, plastic or another transparent material. This plate is provided with a metal film on one of its surfaces. A dielectric film is attached to the metal film. On this surface streptavidin is coated.

A biotinylated 20-mer oligonucleotide having the sequence from Val 9 to Gly 15 of N-ras (RB 671A in the sequence listing) at 1 μM in immobilization buffer comprising 10 mM Tris-HCl, pH 7.5, 0.3 M NaCl, 1 mM EDTA, pH 8.0, was flowed over the sensor chip surface at a flow rate of 5 μl/min at a temperature of 25° C. Then 45 μl of a μM 20-mer oligonucleotide having a complementary sequence (681C in the sequence listing) or a single mismatched base (683C in the sequence listing) was flowed over the immobilized oligonucleotide at a flow rate of 5 μl/min at 25° C. to form a double-stranded oligonucleotide on the sensor chip surface by hybridization. The latter double stranded oligonucleotide had G/T mispairing. For the hybridization a buffer containing 0.9 M NaCl and 90 mM sodium citrate was used.

Mismatch Detection According to the State of the Art 100 nM MutS ($E.coli$ Mismatch Binding Protein from Amersham International) in a binding buffer comprising 50 mM Hepes-KOH, pH 7.2, 100 mM KCl, 1 mM EDTA, pH 8.0, 1 mM dithiothreitol, 5 mM $MgCl_2$ was flowed over the immobilized complementary or G/T mismatched double stranded oligonucleotide and also over the immobilized single-stranded oligonucleotide at a flow rate of 5 μl/min at 25° C.

The binding of MutS was detected in a BIAcore® instrument with registration of the SPR. As shown in FIG. 1A, the increased curve of the sensorgram expressing the binding of MutS to the DNA indicates an increase in relative resonance units due to binding of MutS not only to the mismatched double stranded DNA but also to the single stranded DNA and the complementary double stranded DNA.

EXAMPLE 2

Immobilization and formation of duplex was made in the same manner as in example 1.

Mismatch Detection According to the State of the Art but Modified with Single-strand Binding Protein 45 µl of 50 µg/ml of single-strand binding protein (*E.coli* Single-Strand Binding Protein with mol weight 19 kDa from Pharmacia Biotech)in binding buffer containing 0.005% Tween20 was flowed over the sensor chip containing immobilized strands at a flow rate of 5 µl/min at 25° C. MutS was then applied in the same manner as above.

The binding of MutS was detected in the same way as in example 1. The resulting sensorgram indicated that single-strand binding protein clearly prevents binding of MutS to single stranded DNA. However, MutS still binds to mismatched and non-mismatched oligonucleotides, see FIG. 1B.

EXAMPLE 3:

Immobilization and formation of duplex was made in the same manner as in example 1.

Mismatch Detection According to the Invention

The blocking of single stranded DNA was made in the same way as in example 2.

MutS was incubated for 5 minutes at 250°C. in the presence of 20 mM ATP before use. The ATP incubated MutS was flowed over the immobilized oligonucleotides in the same manner as FIG. 1A.

The detection in the same way as in example 1 showed that mutS previously incubated with ATP bound only to mismatched DNA and not to non-mismatched DNA, see FIG. 2.

Examples with all the 20 mer oligonucleotides in the sequence list and immobilized and hybridized as in table 2 in the sequence listing, showed that all mismatches could be detected with the method according to the invention, see FIG. 3.

TABLE 1

Sequences of 20mer oligonucleotides

| Name | | Sequence | |
|------|---|---------|---|
| | 5' | | 3' |
| RB651A | Biotin- | ACAGCTGGACAAGAAGAGTA | |
| 661T | | TACTCTTCTTGTCCAGCTGT | |
| 662T | | TACTCTTCT<u>A</u>GTCCAGCTGT | |
| 664T | | TACTCTTCT<u>C</u>GTCCAGCTGT | |
| 665T | | TACTCTTCTT<u>C</u>TCCAGCTGT | |
| 666T | | TACTCTTCTT<u>T</u>TCCAGCTGT | |
| RB671A | Biotin- | GTTGGAGCAGGTGGTGTTGG | |
| 681C | | CCAACACCACCTGCTCCAAC | |
| 682C | | CCAACACCA<u>G</u>CTGCTCCAAC | |
| 683C | | CCAACACCA<u>T</u>CTGCTCCAAC | |
| 684C | | CCAACACCA<u>A</u>CTGCTCCAAC | |
| 689C | | CCAACACC<u>T</u>CCTGCTCCAAC | |

The mismatched bases are underlined in the sequence.

TABLE 2

Pairs of oligonucleotides to form immobilized dsDNA

| dsDNA | Immobilized oligonucleotides | Hybridized oligonucleotides |
|-------|------------------------------|-----------------------------|
| non-mismatched dsDNA | RB651A | 661T |
| non-mismatched dsDNA | RB651A | 681C |
| A/A mismatched dsDNA | RB651A | 662T |
| A/C mismatched dsDNA | RB651A | 664T |
| C/C mismatched dsDNA | RB651A | 665T |
| T/C mismatched dsDNA | RB651A | 666T |
| G/G mismatched dsDNA | RB651A | 682C |
| G/T mismatched dsDNA | RB651A | 683C |
| G/A mismatched dsDNA | RB651A | 684C |
| T/T mismatched dsDNA | RB651A | 689C |

What is claimed is:

1. A method for detecting a mutated from a non-mutated sequence of a target polynucleotide in a sample, by using a mismatch binding protein, comprising:
   a) providing non-mutated and mutated target polynucleotide,
   b) forming duplex of the non-mutated and mutated single strands of the target polynucleotide in a) to form a polynucleotide mixture,
   c) adding a single strand binding protein to the polynucleotide mixture from b) whereby said single stranded binding protein binds any unpaired strands in the polynucleotide mixture,
   d) incubating a mismatch binding protein with an activating agent,
   e) adding the incubated mismatch binding protein from d) to the polynucleotide from c), whereby the mismatch binding protein binds to the duplex formed by one non-mutated and one mutated single strand of the target polynucleotide,
   f) detecting the presence of any mismatch binding protein bound to the target polynucleotide.

2. A method according to claim 1, characterized in that before the duplex in step b) is formed, the mutated or the non-mutated target polynucleotide is immobilized to a solid support.

3. A method according to claim 1, characterized in that after the duplex is formed in step b) the target polynucleotide is immobilized to a solid support.

4. A method according to claim 1, characterized in that the mismatch binding protein is immobilized on a solid support and the duplex is introduced and binding of the target polynucleotide is detected.

5. A method according to claim 2, characterized in that the solid support is a sensor chip surface.

6. A method according to claim 5, characterized in that the presence of mismatch binding protein is detected by a label free technique.

7. A method according to claim 6, characterized in that the label free technique is surface plasmon resonance.

8. A method according to claim 2, characterized in that the non-mutated target polynucleotide is immobilized on the solid support.

9. A method according to claim 2, characterized in that the polynucleotide is immobilized by a binding pair, one member of the binding pair being attached to the polynucleotide and the other member being coated on the solid support.

10. A method according to claim 4, characterized in that the mismatch binding protein is immobilized by a binding pair, one member of the binding pair being attached to the mismatch binding protein and the other member of the binding pair being coated on the solid support.

11. A method according to claim 1, characterized in that the mismatch binding protein is one of MutS, HexA, MSH1-6, Rep3, RNaseA, uracil-DNA glycosilase, T4 endonuclease VII, resolvase.

12. A method according to claim 1, characterized in that the activating agent in step
   d) is one of the compounds ATP, ADP, ATP-y-S, AMP-PNP or a nucleotide which can bind to the mismatch binding protein.

13. A method according to claim 1, characterized in that the target polynucleotide in the sample is amplified before step a).

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: synthetic construct

<400> SEQUENCE: 1
acagctggac aagaagagta            20

<210> SEQ ID NO 2
<211> LENGTH: 20
<212> TYPE: DNA
<213> ORGANISM: synthetic construct

<400> SEQUENCE: 2
tactcttctt gtccagctgt            20

<210> SEQ ID NO 3
<211> LENGTH: 20

```
<212> TYPE: DNA
<213> ORGANISM: synthetic construct

<400> SEQUENCE: 3
tactcttcta gtccagctgt                                                    20

<210> SEQ ID NO 4
<211> LENGTH: 20
<212> TYPE: DNA
<213> ORGANISM: synthetic construct

<400> SEQUENCE: 4
tactcttctc gtccagctgt                                                    20

<210> SEQ ID NO 5
<211> LENGTH: 20
<212> TYPE: DNA
<213> ORGANISM: synthetic construct

<400> SEQUENCE: 5
tactcttctt ctccagctgt                                                    20

<210> SEQ ID NO 6
<211> LENGTH: 20
<212> TYPE: DNA
<213> ORGANISM: synthetic construct

<400> SEQUENCE: 6
tactcttctt ttccagctgt                                                    20

<210> SEQ ID NO 7
<211> LENGTH: 20
<212> TYPE: DNA
<213> ORGANISM: synthetic construct

<400> SEQUENCE: 7
gttggagcag gtggtgttgg                                                    20

<210> SEQ ID NO 8
<211> LENGTH: 20
<212> TYPE: DNA
<213> ORGANISM: synthetic construct

<400> SEQUENCE: 8
ccaacaccac ctgctccaac                                                    20

<210> SEQ ID NO 9
<211> LENGTH: 20
<212> TYPE: DNA
<213> ORGANISM: synthetic construct

<400> SEQUENCE: 9
ccaacaccag ctgctccaac                                                    20

<210> SEQ ID NO 10
<211> LENGTH: 20
<212> TYPE: DNA
<213> ORGANISM: synthetic construct

<400> SEQUENCE: 10
ccaacaccat ctgctccaac                                                    20

<210> SEQ ID NO 11
```

-continued

```
<211> LENGTH: 20
<212> TYPE: DNA
<213> ORGANISM: synthetic construct

<400> SEQUENCE: 11
ccaacaccaa ctgctccaac                                                    20

<210> SEQ ID NO 12
<211> LENGTH: 20
<212> TYPE: DNA
<213> ORGANISM: synthetic construct

<400> SEQUENCE: 12
ccaacacctc ctgctccaac                                                    20
```